(12) United States Patent
Dalal et al.

(10) Patent No.: US 11,874,262 B2
(45) Date of Patent: Jan. 16, 2024

(54) METHOD AND APPARATUS FOR PRODUCING A HIGH PRECISION BLENDED GAS MIXTURE COMPRISING A VOLATILE ANALYTE

(71) Applicant: Automotive Coalition For Traffic Safety, Inc., Sterling, VA (US)

(72) Inventors: Neeraj Dalal, Marlborough, MA (US); Brian E. Fratto, Marlborough, MA (US); Kelly Ozdemir, Marlborough, MA (US); Abdullatif Zaouk, Marlborough, MA (US); Michael Willis, Marlborough, MA (US); Clair Strohl, Emmaus, PA (US)

(73) Assignee: Automotive Coalition For Traffic Safety, Inc., Sterling, VA (US)

( * ) Notice: Subject to any disclaimer, the term of this patent is extended or adjusted under 35 U.S.C. 154(b) by 515 days.

(21) Appl. No.: 17/008,072

(22) Filed: Aug. 31, 2020

(65) Prior Publication Data
US 2021/0063367 A1 Mar. 4, 2021

Related U.S. Application Data

(60) Provisional application No. 62/894,038, filed on Aug. 30, 2019.

(51) Int. Cl.
*G01N 33/00* (2006.01)
*B01F 15/04* (2006.01)
(Continued)

(52) U.S. Cl.
CPC ......... *G01N 33/0016* (2013.01); *B01F 23/12* (2022.01); *B01F 23/20* (2022.01);
(Continued)

(58) Field of Classification Search
CPC . B01F 15/0441; B01F 23/20; G01N 33/0016; G01N 33/497
See application file for complete search history.

(56) References Cited

U.S. PATENT DOCUMENTS

| 3,665,748 A | 5/1972 | Mator |
| 5,728,927 A | 3/1998 | Ong |

(Continued)

FOREIGN PATENT DOCUMENTS

| CN | 105021777 | 8/2016 |
| CN | 106645587 | 5/2017 |

(Continued)

OTHER PUBLICATIONS

Department of Transportation—National Highway Traffic Safety Administration (NHTSA), Highway Safety Programs; Model Specifications for Calibrating Units for Breath Alcohol Testers; Conforming Products List of Calibrating Units for Breath Alcohol Testers, Calibrating Units (CU) Model Specifications, Federal Register, vol. 72, No. 121, Jun. 25, 2007, pp. 34742-34748.

*Primary Examiner* — Robert A Hopkins
(74) *Attorney, Agent, or Firm* — Pandiscio & Pandiscio

(57) ABSTRACT

A system for producing a high precision blended gas product (BGP), the system comprising: a supply of a volatile analyte in liquid form; a supply of an inert carrier gas; a supply of at least one diluent gas; an analyte gasifier (AG) subsystem for receiving the volatile analyte in liquid form, nebulizing the volatile analyte and mixing the nebulized volatile analyte with the inert carrier gas so as to form an analyte gas stream (AGS); and a gas mixer (GM) subsystem for receiving the AGS from the AG subsystem and mixing the AGS with the supply of at least one diluent gas so as to produce the BGP, wherein the GM subsystem comprises: a gas analyzer (GA) for receiving the AGS and analyzing the same; a gas proportioner for receiving the AGS from the GA, receiving (Continued)

the at least one diluent gas, and proportioning the AGS and the at least one diluent gas based on the results of the GA so as to provide a proportioned AGS and a proportioned at least one diluent gas; and a gas mixing chamber for receiving the proportioned AGS and the proportioned at least one diluent from the gas proportioner so as to produce the BGP.

31 Claims, 8 Drawing Sheets

(51) Int. Cl.
    *G01N 33/497*     (2006.01)
    *B01F 23/10*     (2022.01)
    *B01F 35/88*     (2022.01)
    *B01F 23/20*     (2022.01)
    *G05D 11/13*     (2006.01)

(52) U.S. Cl.
    CPC ......... *B01F 35/88* (2022.01); *G01N 33/0006* (2013.01); *G01N 33/0047* (2013.01); *G01N 33/497* (2013.01); *G05D 11/132* (2013.01); *B01F 23/19* (2022.01)

(56) References Cited

U.S. PATENT DOCUMENTS

| | | |
|---|---|---|
| 5,731,508 A | 3/1998 | Slemeyer |
| 6,166,379 A | 12/2000 | Montaser et al. |
| 7,845,206 B2 | 12/2010 | Wohltjen |
| 9,709,582 B1 | 7/2017 | Gordon et al. |
| 2003/0112431 A1 | 6/2003 | Ketkar |
| 2007/0102533 A1 | 5/2007 | Rosell et al. |
| 2014/0230518 A1 | 8/2014 | Lueck et al. |
| 2015/0160190 A1 | 6/2015 | Ravishankar |
| 2018/0252699 A1 | 9/2018 | Dang |
| 2019/0250184 A1* | 8/2019 | Collins .............. G01N 33/0057 |

FOREIGN PATENT DOCUMENTS

| | | |
|---|---|---|
| SE | 531741 W | 7/2009 |
| WO | WO 2019/115473 | 6/2019 |

\* cited by examiner

METHOD AND APPARATUS FOR PRODUCING A HIGH PRECISION BLENDED GAS MIXTURE COMPRISING A VOLATILE ANALYTE

REFERENCE TO PENDING PRIOR PATENT APPLICATION

This patent application claims benefit of U.S. Provisional Patent Application Ser. No. 62/894,038, filed Aug. 30, 2019 by Automotive Coalition For Traffic Safety, Inc. and Brian E. Fratto et al. for METHOD AND APPARATUS FOR PRODUCING HUMIDIFIED, CONTROLLED VOLATILE EFFLUENTS USING REAL-TIME FEEDBACK CONTROLS, which patent application is hereby incorporated herein by reference.

FIELD OF THE INVENTION

This invention relates generally to methods and apparatus for producing blended gas mixtures, and more particularly to methods and apparatus for producing high precision blended gas mixtures comprising volatile analytes.

BACKGROUND OF THE INVENTION

Today various detectors are used to measure the concentration of specific gas components in a person's breath.

By way of example but not limitation, one type of detector is designed to measure the concentration of ammonia in a person's breath, since there is evidence to suggest that the presence of ammonia in a person's breath is correlated with certain diseases such as high blood pressure, diabetes, and cancer. Thus, a detector that is capable of measuring low concentrations of ammonia may provide an early indication of a disease, so that a person could receive early treatment for the disease.

By way of further example but not limitation, another type of detector is designed to measure the concentration of carbon dioxide and oxygen in a person's breath. This type of detector may be used in a hospital setting to monitor a person's respiratory function when they are sick or injured.

Still another type of detector, commonly called a breathalyzer, is designed to measure the concentration of alcohol in a person's breath (i.e., to measure a person's breath alcohol content, which is sometimes referred to as "BrAC"). It will be appreciated that an alcohol detection system, integrated into a vehicle, could prevent a person from operating the vehicle when their BrAC is above a legal limit. An example of this type of alcohol detection system is the Driver Alcohol Detection System for Safety program (www.dadss.org), sometimes referred to herein as "the DADSS program".

Thus it will be appreciated that there are numerous situations in which it may be desirable to use a detector to measure the concentration of specific gas components in a person's breath.

Depending on the application, the accuracy and precision of the detector can be critical. By way of example but not limitation, for the DADSS program, the detector must be able to detect a person's BrAC with great accuracy and precision, e.g., a precision as small as 0.0003% of the BrAC level.

In order to calibrate and test the performance of such a detector, it is necessary to be able to produce a gas mixture of known components, where the concentrations of the components are established with sufficient accuracy and precision. In addition, where the gas mixture is intended to mimic exhaled human breath, the gas mixture must be appropriately humidified.

Thus there is a need for an apparatus that is capable of producing a high precision blended gas mixture comprising a volatile analyte, sometimes referred to herein as a "blended gas product" or "BGP", wherein the apparatus is able to maintain accurate and precise concentrations of the constituent components of the BGP for extended periods of time while also providing the ability to change the concentrations of the constituent components of the BGP on demand.

And there is a need for the apparatus to be capable of producing a humidified BGP.

And there is a need for the apparatus to be capable of producing a BGP which mimics an exhaled human breathe containing a volatile analyte (e.g., for testing high performance breath sensors, such as detectors in the DADSS program for determining a person's BrAC).

In practice, previous attempts to provide such a system have been unsatisfactory, due to the limited precision and accuracy of prior art systems.

More particularly, the commercial gas industry typically provides gases with a compositional accuracy of ±2% of the reported concentration. This limits the accuracy of a gas mixture produced with component gases which are obtained through commercial sources.

In addition, since volatile analyte gases (e.g., ethanol, sometimes referred to herein as "EtOH") supplied by commercial sources are typically supplied in tanks with the volatile analyte gases being mixed in an inert gas (e.g., helium), gas physics dictate a high frequency of tank turnover (i.e., tank replacements), and hence results in the possibility of additional variability and high cost. More particularly, the volatile analyte gas must be significantly diluted in the inert gas in order to stay in the gas phase. This limitation in analyte gas concentration increases the rate at which tanks are depleted, resulting in a high frequency of tank changes, and hence high costs. In addition, the need for such frequent tank changes is detrimental to long term testing, where precise streams of volatile analyte gases must be produced for an extended period of time, since such tank changes introduce the possibility of additional variability during testing.

In addition to the foregoing, where the gas mixture being produced must mimic human breath, the gas mixture must be humidified prior to being used for testing. Due to miscibility and solubility issues, in some circumstances it is very difficult to create a homogenized gas mixture which contains both a volatized component (e.g., ethanol) as well as a humidity level that is reaching its temperature-dependent solubility limit. Current technologies such as wet bath (bubbler) systems are limited by the physical principles of miscibility in the organic compounds that are to be volatized. An example of this may be found in toluene. When toluene is volatized in a traditional aqueous bubbler, the toluene will sit as a bilayer on the surface of the denser aqueous layer, thus inhibiting the ability to create a homogeneous gas mixture. Furthermore, the manner in which the humidification is undertaken can be critical. If the humidification is undertaken too early in the process, the gas mixture may be compromised and an inaccurate concentration of analyte may be created. In other circumstances, if the humidification is undertaken too late in the process, the system can be susceptible to temperature changes which may result in the nucleation of either organic or aqueous droplets which may then scavenge components of the homogeneous gas out of solution, thereby creating a course colloidal aerosol instead of a uniform and fine nebulized analyte.

The foregoing considerations apply to the general problem of producing humidified high precision blended gas mixtures comprising volatile analytes.

Further understanding can be gained by considering the problem of producing humidified high precision blended gas mixtures comprising ethanol, such as those required for calibrating and testing breath-based alcohol detectors.

More particularly, when testing breath-based alcohol detectors, an earlier generation apparatus was created for producing humidified blended gas mixtures using commercially supplied ethanol gas tanks (this earlier generation apparatus is sometimes referred to as "the Wet Gas Breath Alcohol Simulator", or "WGBAS"). The WGBAS has shown that it is able to produce a wet breath ethanol mixture that is able to meet and exceed the degree of precision required by the DADSS program (e.g., a BrAC level that does not vary more than 0.0075% of the target BrAC level). However, the method by which the ethanol gas mixture is produced in the WGBAS apparatus yields an ethanol gas mixture which cannot be maintained with precision and accuracy for an extended and useful period of time. Since the concentrations of the component gases in a gas mixture contained in a tank cannot be increased after the tank is filled, the WGBAS apparatus utilizes a high concentration ethanol tank. The ethanol from this tank is then combined with a carrier gas (e.g., helium, nitrogen, or other non-reactive gas), and mass flow controllers (MFCs) are used to produce an ethanol gas mixture of a final concentration. Due to the physical properties of ethanol, a 3000 ppm ethanol gas mixture must be kept at a low pressure in order to ensure that the ethanol stays in the gaseous state. This low pressure means that a tank containing the ethanol gas mixture necessarily contains a relatively small quantity of ethanol, thus creating the situation where tanks must be changed constantly during testing in order to provide the desired quantity of ethanol in the ethanol gas mixture.

Furthermore, changing tanks during testing creates consistency issues during testing, e.g., due to the ±2% variation of the reported concentration which is typical in the commercial gas industry. This introduction of error causes the need for constant monitoring and supervision in order to ensure that a calibration or test cycle is not voided due to the use of multiple ethanol tanks which may provide different mixtures (and hence provide different ethanol concentrations in the final gas output of the WGBAS apparatus).

In addition to the foregoing, current technologies for creating humidified, controlled ethanol gas mixtures (such those listed in the "DEPARTMENT OF TRANSPORTATION National Highway Traffic Safety Administration Highway Safety Programs; Model Specifications for Calibrating Units for Breath Alcohol Testers; Conforming Products List of Calibrating Units for Breath Alcohol Testers") have limitations including (i) the maximum achievable accuracy and precision of the humidified ethanol gas mixture, and (ii) the length of time that a constant ethanol concentration can be maintained. More particularly, the technologies listed in the NHTSA Model Specification are either so-called "Dry Gas systems" or "Wet Bath ("bubbler") systems". Dry Gas systems consist of tanks of ethanol gas with a carrier gas (e.g., nitrogen). As noted above, typical gas systems come with an analytical accuracy of ±2% of the reported concentration. Since component gases are supplied by commercial sources are supplied in tanks, gas physics dictate a high frequency of tank turnover (i.e., tank replacement), and hence results in (i) decreased precision when using more than one tank for a calibration or test, and (ii) high cost. Wet Bath ("bubbler") systems consist of a heated bath containing a standardized alcohol water solution which an inert carrier gas is passed through. This "bubbling" action creates a gas phase mixture of humidified ethanol and carrier gas. Wet Bath systems provide a humidified controlled gas ethanol analyte, however, the accuracy and precision of these systems is limited. The NHTSA model standard requires only that these systems have a standard error of less than 0.002% of the BrAC level ("accuracy") and a relative standard deviation (RSD) of 2% ("precision"). These accuracy and precision requirements are an order of magnitude less accurate and precise than the DADSS program requirements. In addition, Wet Bath systems are known to be incapable of maintaining a constant ethanol concentration because the concentration of the ethanol in the gas phase decreases as the ethanol in the liquid standard solution is used up. And, both Dry Gas and Wet Bath systems cannot be easily or accurately adjusted on demand. The ethanol concentration in a Dry Gas system cannot change after the tank has been produced, and the ethanol concentration in a Wet Bath system can only be grossly adjusted on demand, but not accurately, precisely, and/or quickly adjusted on demand.

As a result, there is a need for a new and improved method and apparatus for producing a high precision blended gas mixture comprising a volatile analyte, sometimes referred to herein as a "blended gas product" or "BGP, wherein the method and apparatus are able to maintain accurate and precise concentrations of the constituent components of the BGP for extended periods of time while also providing the ability to change the concentrations of the constituent components of the BGP on demand.

And there is a need for a new and improved method and apparatus for producing a humidified BGP.

And there is a need for a new and improved method and apparatus for producing a BGP which mimics an exhaled human breath containing a volatile analyte (e.g., for testing high performance breath sensors, such as detectors in the DADSS program for determining a person's BrAC).

SUMMARY OF THE INVENTION

The present invention comprises the provision and use of a new and improved method and apparatus for producing a high precision blended gas mixture comprising a volatile analyte, sometimes referred to herein as a "blended gas product" or "BGP", wherein the method and apparatus are able to maintain accurate and precise concentrations of the constituent components of the BGP for extended periods of time while also providing the ability to change the concentrations of the constituent components of the BGP on demand.

The present invention also comprises a new and improved method and apparatus for producing a humidified BGP.

And the present invention also comprises a new and improved method and apparatus for producing a BGP which mimics an exhaled human breath containing a volatile analyte (e.g., for testing high performance breath sensors, such as detectors for determining a person's BrAC).

In one preferred form of the invention, the apparatus for producing a high precision blended gas mixture comprising a volatile analyte (i.e., the "blended gas product" or "BGP") utilizes a combination of two subsystems to create the BGP: (i) an analyte gasifier (AG) subsystem which takes a volatile analyte in liquid form, nebulizes the volatile analyte and mixes the nebulized volatile analyte with an inert carrier gas so as to produce an analyte gas stream, sometimes referred to herein as an "AGS", and (ii) a gas mixer (GM) subsystem which mixes the AGS with other gases, and which also provides humidification to the AGS, so as to produce a BGP at a desired concentration with high accuracy and precision.

The analyte gasifier (AG) subsystem uses the thermodynamic principals of vaporization to rapidly convert a desired volatile analyte (e.g., ethanol) into its gaseous state. This formation of the desired analyte vapor (e.g., ethanol vapor) is carried out in the presence of a constant flow of a carrier gas (e.g., helium or an alternative gas that is nonreactive with the desired analyte) that is used to ensure that the concentration of the analyte vapor remains low enough that the analyte remains in a gaseous state. The AGS is then fed to the gas mixer (GM) subsystem.

The gas mixer (GM) subsystem receives the AGS from the analyte gasifier (AG) subsystem and passes the AGS through a gas analyzer (GA), which monitors the concentration of the AGS arriving from the analyte gasifier (AG) subsystem. The gas mixer (GM) subsystem also comprises a gas proportioner. Data from the GA is reported to the gas proportioner, which uses this data to appropriately proportion the flow rates of (i) the AGS based on any change in its analyte concentration, and (ii) one or more diluent gases (e.g., $O_2$, $CO_2$ and $N_2$), sometimes referred to herein when combined as the "combined diluent gas stream" or "CDGS", which are ultimately to be combined with the AGS. The proportioned CDGS exiting the gas proportioner enters a temperature-controlled chamber and is then humidified so as to produce a gas stream sometimes referred to herein as the "humidified combined diluent gas stream" or "HCDGS". The proportioned AGS exiting the gas proportioner and the proportioned HCDGS exiting the humidifier are then combined in a gas mixing tube so as to produce the desired high precision blended gas mixture comprising a volatile analyte (i.e., the BGP).

In one preferred form of the invention, the BGP is passed through a sensor before leaving the gas mixer (GM) subsystem. This sensor monitors the concentration of the various constituents of the BGP. Data from this sensor is sent back to the gas proportioner, which then adjusts the flow rates of (i) the AGS based on its changing analyte concentration, and (ii) the one or more diluent gases (e.g., $O_2$, $CO_2$ and $N_2$), sometimes referred to herein when combined as the "combined diluent gas stream" or "CDGS", which are ultimately to be combined with the AGS, so as to ensure the correct composition of the BGP. Thus, in this form of the invention, the gas mixer (GM) subsystem provides a real-time feedback control which adjusts, in real time, the amounts of the AGS and the CDGS that are used to create, with humidification, the BGP so as to compensate for any variations in the concentration of the AGS being produced by the AG so that the final BGP has a concentration of gases that is both accurate and precise.

In one form of the invention, the gas analyzer (GA) monitors the concentration of the AGS being created in the analyte gasifier (AG) subsystem by comparing the speed of sound through the carrier gas (e.g., helium), which is a known physical constant for that carrier gas, and the speed of sound through the AGS—the difference in the speeds is calculated and used to determine the concentration of the volatile analyte in the AGS.

The output of the gas mixer (GM) subsystem may be used for a variety of purposes. By way of example but not limitation, where the CDGS and humidity are blended so as to mimic exhaled human breath, the BGP may be used for testing high performance breath sensors. By way of further example but not limitation, where the analyte is ethanol, the BGP may be used for testing detectors for determining a person's BrAC.

In one form of the invention, there is provided a system for producing a high precision blended gas product (BGP), the system comprising:
  a supply of a volatile analyte in liquid form;
  a supply of an inert carrier gas;
  a supply of at least one diluent gas;
  an analyte gasifier (AG) subsystem for receiving the volatile analyte in liquid form, nebulizing the volatile analyte and mixing the nebulized volatile analyte with the inert carrier gas so as to form an analyte gas stream (AGS); and
  a gas mixer (GM) subsystem for receiving the AGS from the AG subsystem and mixing the AGS with the supply of at least one diluent gas so as to produce the BGP, wherein the GM subsystem comprises:
    a gas analyzer (GA) for receiving the AGS and analyzing the same;
    a gas proportioner for receiving the AGS from the GA, receiving the at least one diluent gas, and proportioning the AGS and the at least one diluent gas based on the results of the GA so as to provide a proportioned AGS and a proportioned at least one diluent gas; and
    a gas mixing chamber for receiving the proportioned AGS and the proportioned at least one diluent from the gas proportioner so as to produce the BGP.

In another form of the invention, there is provided a method for producing a high precision blended gas product (BGP), the method comprising:
  providing:
    a supply of a volatile analyte in liquid form;
    a supply of an inert carrier gas; and
    a supply of at least one diluent gas;
  nebulizing the volatile analyte and mixing the nebulized volatile analyte with the inert carrier gas so as to form an analyte gas stream (AGS); and
  mixing the AGS with the supply of at least one diluent gas so as to produce the BGP, wherein the mixing comprises:
    analyzing the AGS;
    proportioning the AGS and the at least one diluent gas based on the results of analyzing the AGS so as to provide a proportioned AGS and a proportioned at least one diluent gas; and
    mixing the proportioned AGS and the proportioned at least one diluent so as to produce the BGP.

In another form of the invention, there is provided a volatizer for receiving volatile analyte in liquid form, nebulizing the volatile analyte and mixing the nebulized volatile analyte with an inert carrier gas so as to form an analyte gas stream (AGS), the volatizer comprising:
  a first tube configured to receive the volatile analyte in liquid form, the first tube having a first portion comprising a distal end, a proximal end, and a lumen extending therebetween, the first portion of the first tube having an outer surface which tapers inwardly in the distal direction;
  a second tube configured to receive the inert carrier gas, the second tube having a second portion comprising a distal end, a proximal end and a lumen extending therebetween, the second portion of the second tube having an inner surface which steps down from a larger diameter to a smaller diameter;

the second portion of the second tube being disposed coaxially over the first portion of the first tube so that the inner surface of the second portion of the second tube is spaced from the outer surface of the first portion of the first tube; and the distal end of the first portion of the first tube is disposed adjacent to the location at which the inner surface of the second portion of the second tube steps down from a larger diameter to a smaller diameter.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
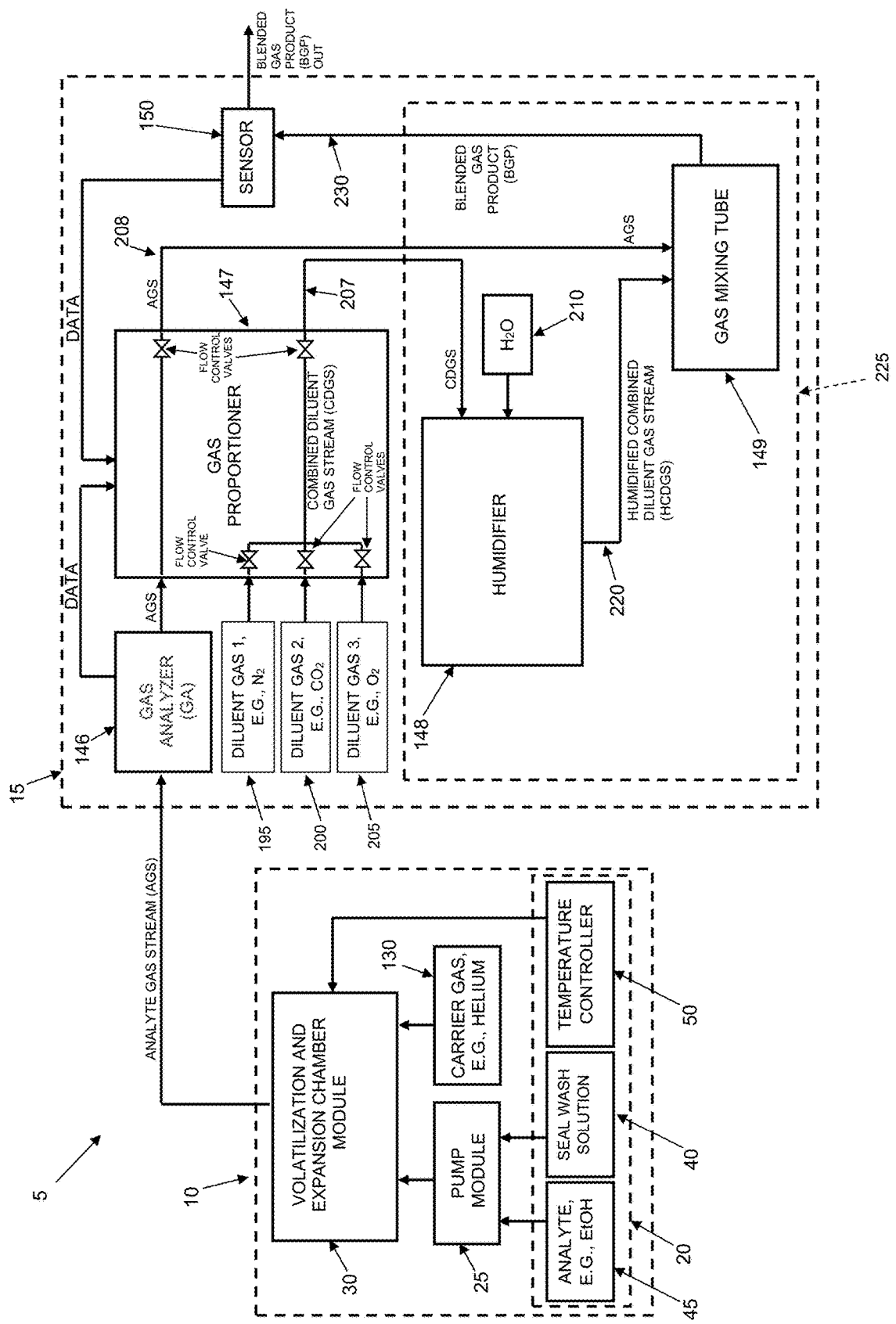
FIG. 1 is a schematic view showing novel apparatus for producing a high precision blended gas mixture comprising a volatile analyte, sometimes referred to herein as a "blended gas product" or "BGP", wherein the novel apparatus comprises two subsystems: (i) an analyte gasifier (AG) subsystem which takes a volatile analyte in liquid form, nebulizes the volatile analyte and mixes the nebulized analyte with an inert carrier gas so as to produce an analyte gas stream, sometimes referred to herein as an "AGS", and (ii) a gas mixer (GM) subsystem which mixes the AGS with other gases, and which also provides humidification to the AGS, so as to produce a BGP at a desired concentration with high accuracy and precision.
Figure 2:
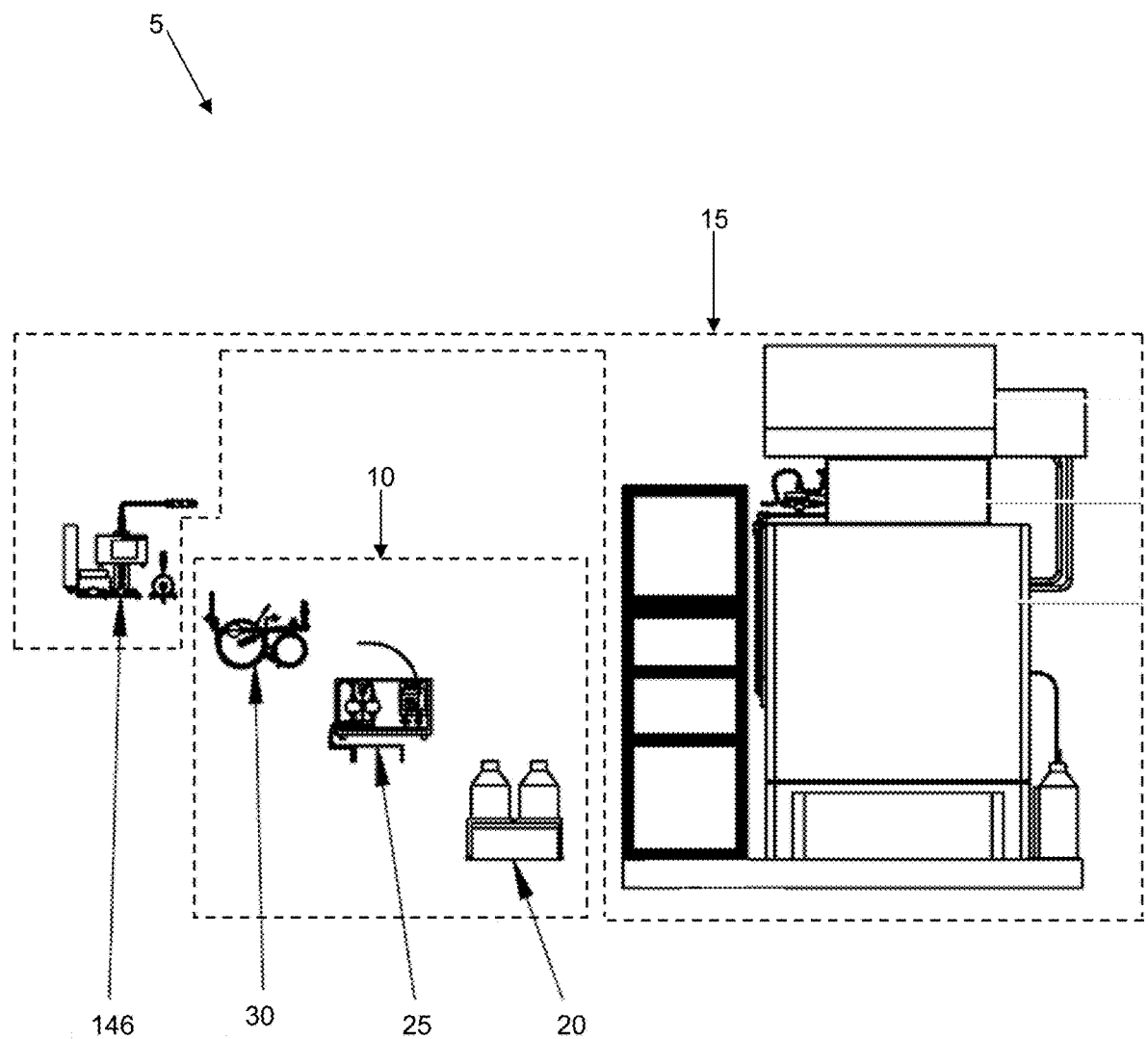
FIG. 2 is a schematic view showing the novel apparatus for producing a BGP, wherein the analyte gasifier (AG) subsystem is shown in exploded view, and also showing the gas analyzer (GA) exploded from the gas mixer (GM) subsystem.

Looking first at FIGS. 1 and 2, there is shown novel apparatus 5 for producing a high precision blended gas mixture comprising a volatile analyte (i.e., the "blended gas product" or "BGP"), wherein the BGP may be used for a variety of purposes. By way of example but not limitation, where the diluent gases and humidity are blended to mimic exhaled human breath, the BGP may be used for testing high performance breath sensors. By way of further example but not limitation, where the analyte is ethanol, the BGP may be used for testing detectors for determining a person's BrAC.

For improved understanding, apparatus 5 will sometimes hereinafter be discussed in the context of its use to produce a humidified BGP which mimics a human exhaled breath, and where the analyte is ethanol, e.g., such as BGPs required for calibrating and testing breath-based alcohol detectors such as the alcohol detectors provided by the DADSS program. However, such application of apparatus 5 is intended to be merely exemplary, and should not be construed as limiting the invention to the production of BGPs which mimic a human exhaled breath and/or where the analyte is ethanol—the present invention is capable of producing a wide range of BGPs of various compositions and comprising various volatile analytes.

Novel apparatus 5 generally comprises two subsystems: (i) an analyte gasifier (AG) subsystem 10 which takes a volatile analyte in liquid form, nebulizes the volatile analyte and mixes the nebulized volatile analyte with an inert carrier gas so as to produce an analyte gas stream, sometimes referred to herein as an "AGS", and (ii) a gas mixer (GM) subsystem 15 which mixes the AGS with other gases, and which also provides humidification to the AGS, so as to produce a BGP at a desired concentration with high accuracy and precision.

Analyte Gasifier (AG) Subsystem 10

Analyte gasifier (AG) subsystem 10 takes a volatile analyte in liquid form, nebulizes the volatile analyte and mixes the nebulized volatile analyte with an inert carrier gas so as to produce an analyte gas stream, sometimes referred to herein as an "AGS". The AGS output by analyte gasifier (AG) subsystem 10 is fed to gas mixer (GM) subsystem 15 so as to produce the desired BGP.

Figure 3:
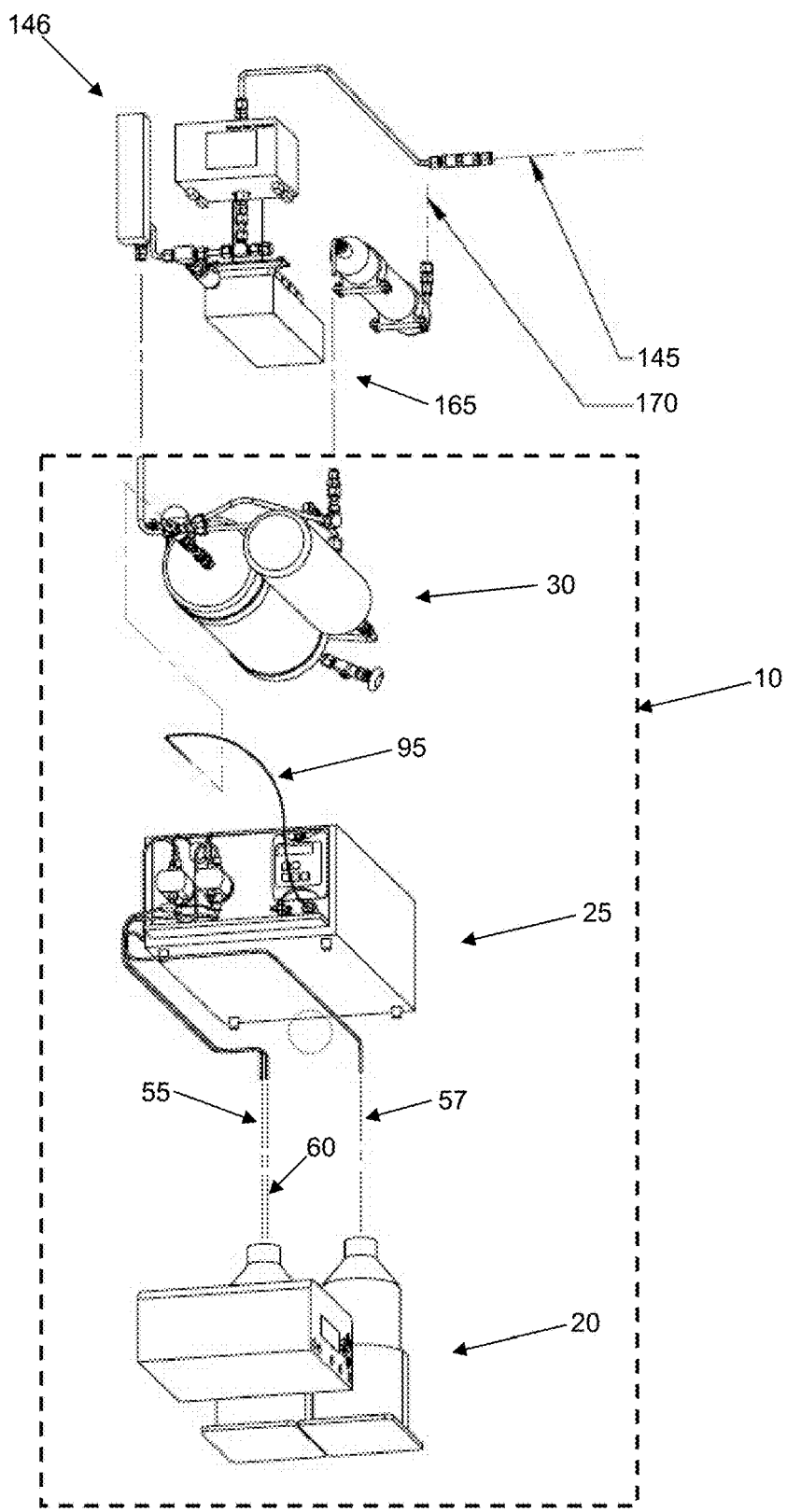
FIG. 3 is a schematic view showing the analyte gasifier (AG) subsystem in greater detail, wherein the analyte gasifier (AG) subsystem generally comprises (a) a reagents and temperature controller module, (b) a pump module, and (c) a volatilization and expansion chamber module, and further showing the gas analyzer (GA) of the gas mixer (GM) subsystem.

Looking now at FIGS. 1-3, analyte gasifier (AG) subsystem 10 generally comprises (a) a reagents and temperature controller module 20, (b) a pump module 25, and (c) a volatilization and expansion chamber module 30.

As will hereinafter be discussed, reagents and temperature controller module 20 is used to (i) supply pump module 25 with the analyte (e.g., ethanol) which is to be nebulized in volatilization and expansion chamber module 30, (ii) supply seal wash solution to pump module 25 (see below), and (iii) modulate the temperature of the volatilization chamber (see below) of volatilization and expansion chamber module 30. Pump module 25 supplies the analyte (e.g., ethanol) to volatilization and expansion chamber module 30. The temperature-controlled volatilization and expansion chamber module 30 receives the analyte (e.g., ethanol) in liquid form, nebulizes the analyte (e.g., ethanol) and mixes the analyte with an inert carrier gas (e.g., helium) so as to produce an analyte gas stream, sometimes referred to herein as an "AGS".

(a) Reagents And Temperature Controller Module 20

Reagents and temperature controller module 20 is used to supply the analyte (e.g., ethanol) and seal wash solution to pump module 25, and reagents and temperature controller module 20 is used to control the temperature of the volatilization chamber (see below) of the volatilization and expansion chamber module 30.

Figure 4:
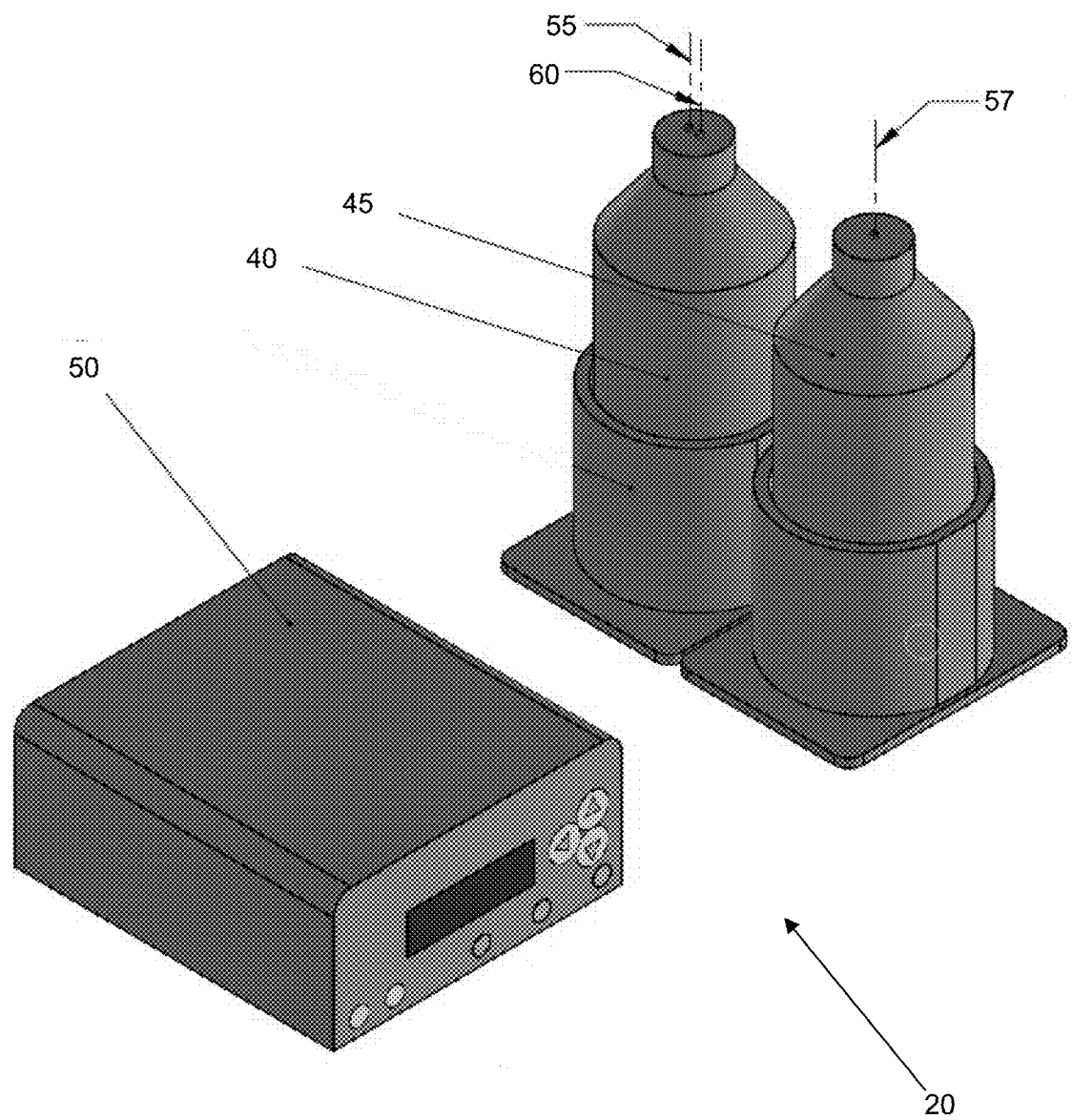
FIG. 4 is a schematic view showing further details of the reagents and temperature controller module.

Reagents and temperature controller module 20 is shown in further detail in FIG. 4. Reagents and temperature controller module 20 generally comprises a seal wash solution supply 40, an analyte (e.g., ethanol) solution supply 45, and a temperature controller 50 for controlling the temperature of the volatilization chamber (see below) of volatilization and expansion chamber module 30. A feed line 55 for seal wash solution supply 40, a feed line 57 for analyte (e.g., ethanol) solution supply 45, and a return line 60 for seal wash solution supply 40 are connected to pump module 25. Feed line 55 provides the seal wash solution to pump module 25 and feed line 57 provides the analyte (e.g., ethanol) to pump module 25. Any seal wash solution returning back from pump module 25 flows through return line 60 into seal wash solution supply 40.

Figure 6:
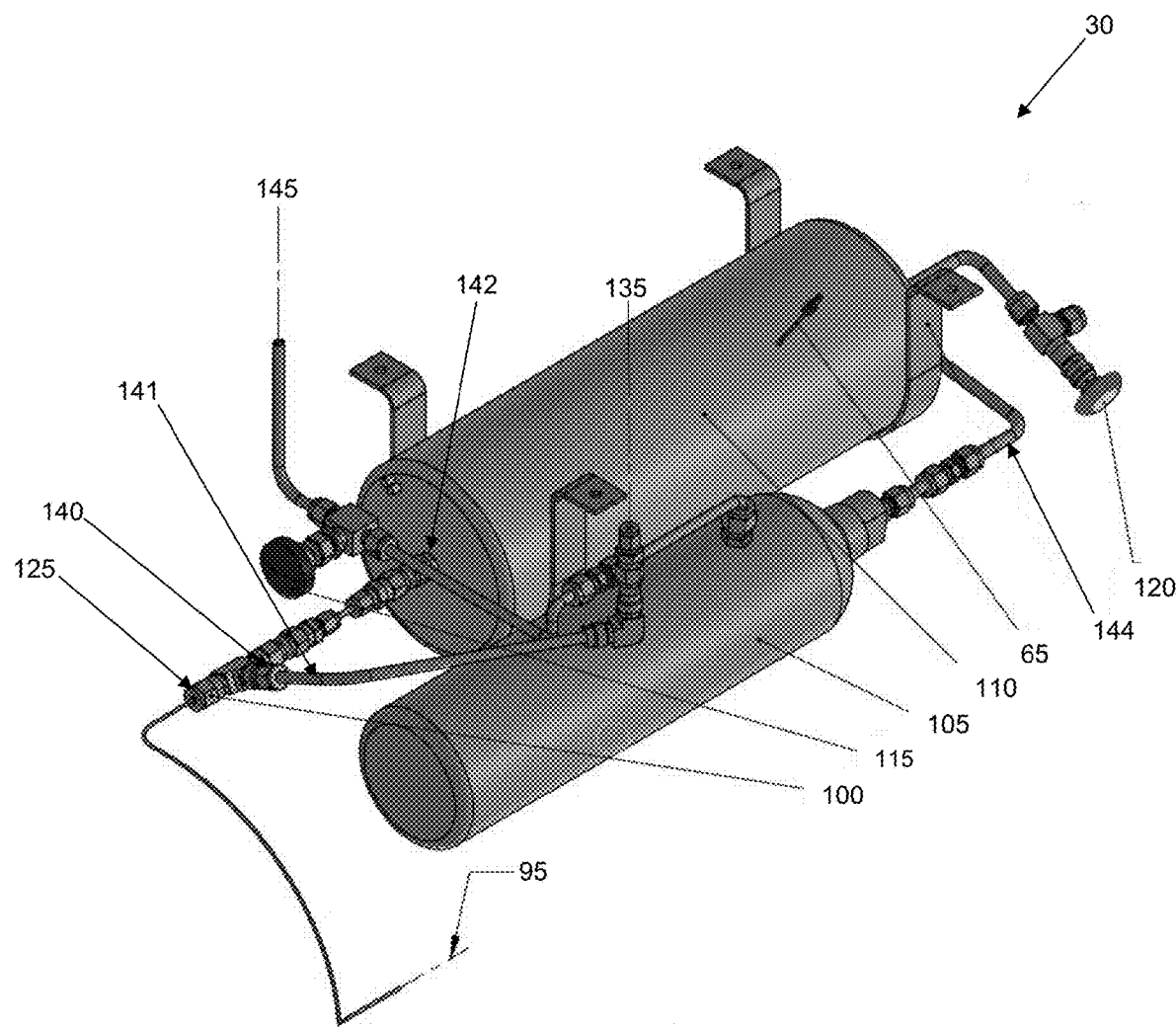
FIG. 6 is a schematic view showing further details of the volatilization and expansion chamber module, wherein the volatilization and expansion chamber module comprises a nebulizer.

Temperature controller 50 (which is preferably connected to a thermocouple 65 in volatilization and expansion chamber module 30, see FIG. 6) is used to maintain the temperature of the volatilization chamber (see below) of volatilization and expansion chamber module 30 at one or more predetermined temperature settings.

(b) Pump Module 25

Figure 5:
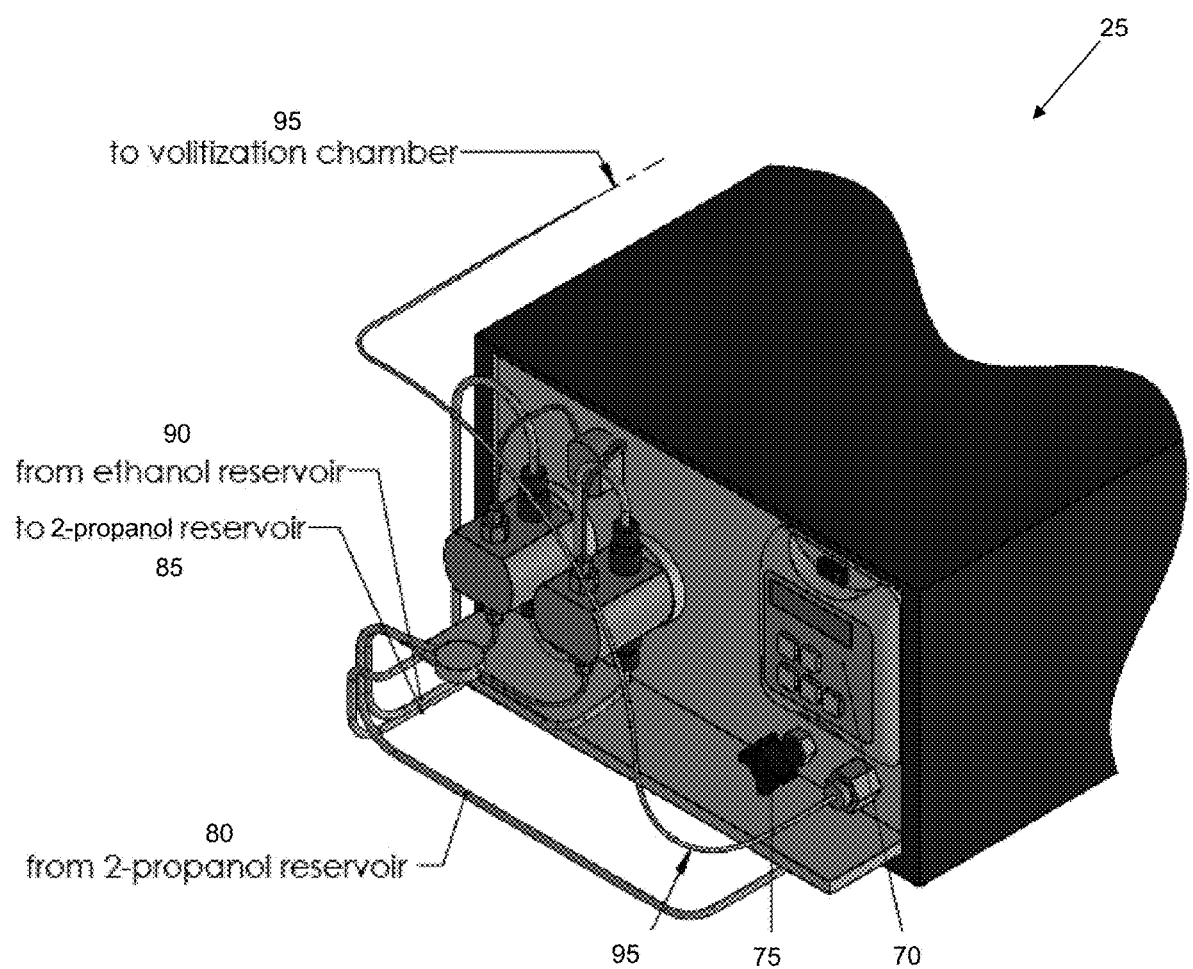
FIG. 5 is a schematic view showing further details of the pump module.

Pump module 25 is used to supply the analyte (e.g., ethanol) to the temperature-controlled volatilization and expansion chamber module 30. Pump module 25 is shown in further detail in FIG. 5. In one preferred embodiment of the present invention, pump module 25 is a high-performance liquid pump. More particularly, the pump used in pump module 25 is preferably an ultra high pressure dual piston pump. The ultra high pressure dual piston pump is of the dual-head type so as to reduce pulsation and ensure a stable flow is presented to volatilization and expansion chamber module 30. Pump module 25 comprises a controller 70 and a knob 75 for priming the high-performance liquid pump.

To prevent contamination and seal failure of the pump, a seal wash solution is used to flush the rear of the pump heads. The seal wash solution may be propanol, another organic seal wash solution or a non-organic seal wash solution. The seal wash solution enters pump module 25 at line 80 (via feed line 55 of reagents and temperature controller module 20) and exits pump module 25 at line 85 (and returns to seal wash solution supply 40 via return line 60 of reagents and temperature controller module 20). Although flushing the rear of the pump heads may not be required due to the non-reactivity of the analyte (e.g., ethanol) with the inner-workings of the pump heads, this preventative measure is believed to be good practice to ensure a reliable working system. Additionally, the presence of a liquid behind the pump heads (i.e., the seal wash solution) helps to isolate vibrations and balance the internal operating pressures within the pump heads.

The analyte (e.g., ethanol) from reagents and temperature controller module 20 enters pump module 25 at line 90 (via feed line 57 of reagents and temperature controller module 20) and exits pump module 25 at line 95 where it is pumped to the volatilization and expansion chamber module 30.

(c) Volatilization and Expansion Chamber Module 30

Volatilization and expansion chamber module 30 is a temperature-controlled unit that receives the analyte (e.g., ethanol) in liquid form, nebulizes the analyte (e.g., ethanol) and mixes the analyte with an inert carrier gas (e.g., helium) so as to produce an analyte gas stream, sometimes referred to herein as an "AGS". Volatilization and expansion chamber module 30 is shown in detail in FIGS. 6-9.

In one preferred embodiment of the present invention, volatilization and expansion chamber module 30 comprises a nebulizer 100, an expansion chamber 105 and a volatilization chamber 110. Volatilization and expansion chamber module 30 may also comprise an adjustment valve 115 and a pressure release mechanism 120. Adjustment valve 115 controls the flow rate of the AGS exiting volatilization and expansion chamber module 30 and passing to gas mixer (GM) subsystem 15. Line 95 takes the analyte (e.g., ethanol) inflowing from pump module 25 and brings it into a first entrance 125 of nebulizer 100. A carrier gas (e.g., helium) is introduced from a carrier gas supply 130 (see FIG. 1) into a fitting 135 which leads into a second entrance 140 of nebulizer 100 via a carrier gas line 141. Line 95 and carrier gas Line 141 enter nebulizer 100 so as to form a "T" joinder. In nebulizer 100, the carrier gas (e.g., helium) introduced via second entrance 140 of nebulizer 100 flows over the liquid analyte (e.g., ethanol) introduced via first entrance 125 of nebulizer 100, thereby introducing the analyte (e.g., ethanol) into volatilization chamber 110 via a fitting 142.

Figure 7:
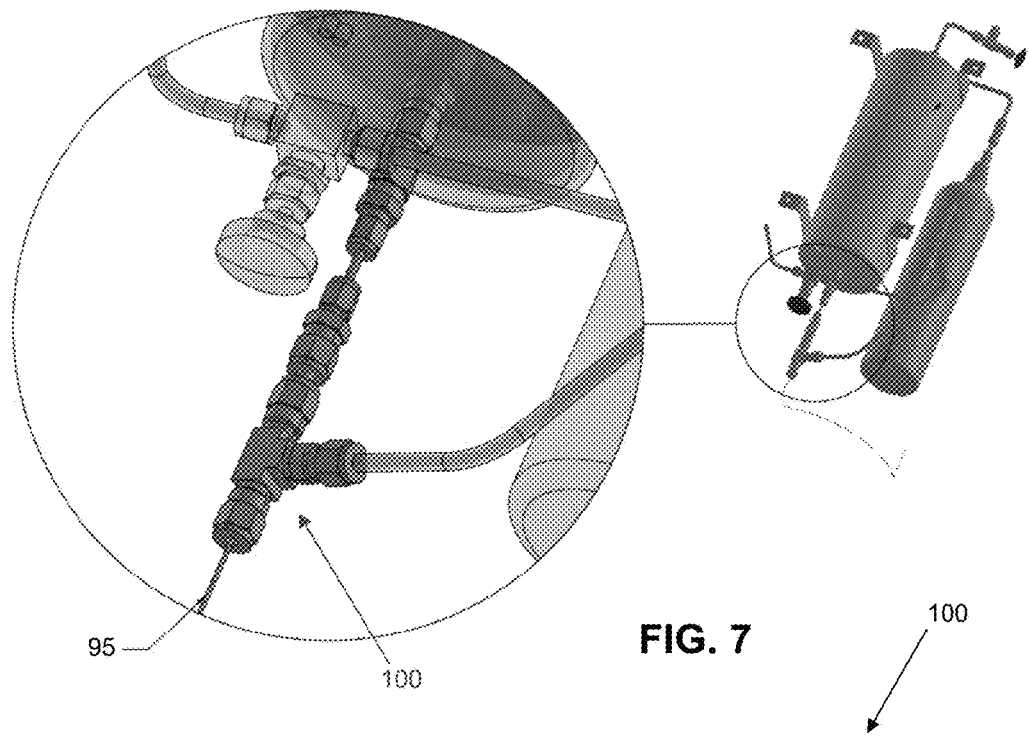
FIGS. 7-9 are schematic views showing further details of the nebulizer of the volatilization and expansion chamber module.
Figure 8:
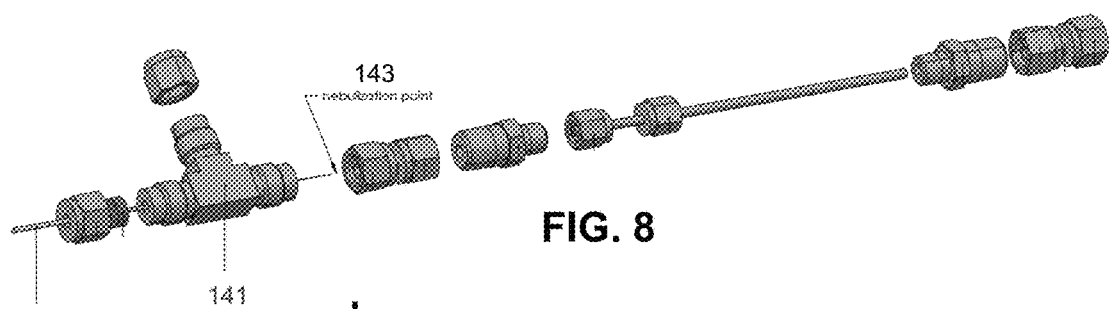
Figure 9:
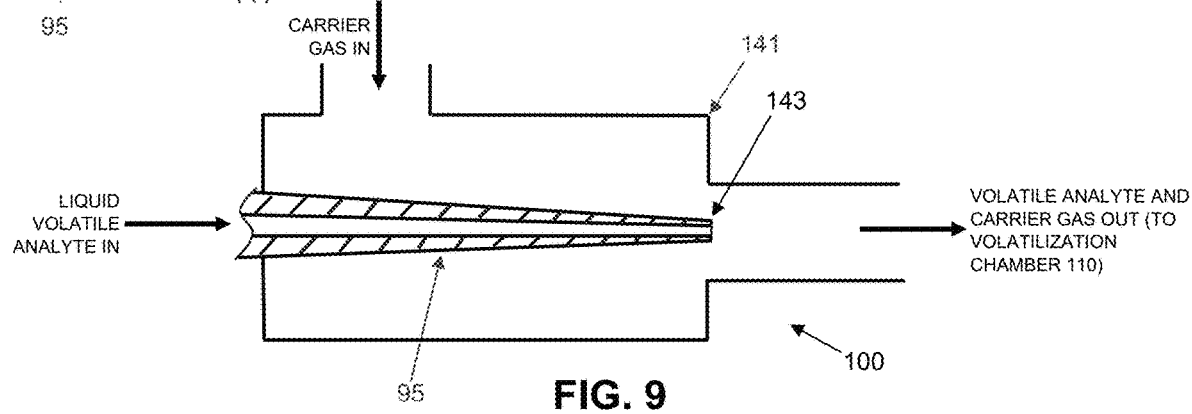

More particularly, and looking now at FIGS. 7-9 which show enlarged views of nebulizer 100 of volatilization and expansion chamber module 30, nebulizer 100 is used to inject a stream of liquid analyte (e.g., ethanol) into a flowing carrier gas stream (e.g., helium), with the mixture of the two streams thereafter passing into temperature-controlled volatilization chamber 110. It should be appreciated that the mixing of the two streams decreases variability in the analyte (e.g., ethanol) concentration by creating a homogenized mixture of analyte (e.g., ethanol) and the carrier gas (e.g., helium) before the mixture enters volatilization chamber 110. The tip of line 95 within nebulizer 100 is honed to a low-angle conical point 143 so as to drastically lower the amount of surface area at the point where the liquid analyte (e.g., ethanol) meets the carrier gas (e.g., helium). Reducing this surface area reduces the capillary attachment of the liquid analyte (e.g., ethanol) to line 95 (which may comprise PEEK tubing or tubing formed out of another material). Combining this conical shape with the accelerated carrier gas (e.g., helium) flow over conical tip 143 of the tubing of line 95 ensures a complete wicking of the liquid analyte (e.g., ethanol) droplets into the carrier gas (e.g., helium).

The introduction of liquid analyte (e.g., ethanol) to the volatilization and expansion chamber module 30 is an important aspect of the design. Without a smooth, pulseless flow of liquid analyte (e.g., ethanol) into volatilization chamber 110, the system will not be able to provide the level of precision required. To permit system 5 to provide the level of precision required, a high precision pump is used to provide a smooth, pulseless flow of liquid analyte (e.g., ethanol) into volatilization chamber 110. In one form of the invention, a high performance dual headed pump is used in pump module 25. More particularly, the pump used in pump module 25 is preferably an ultra high pressure dual piston pump. The ultra high pressure dual piston pump is able to handle a flow rate as low as 0.001 mL/min with a repeatability that is ±0.1%. The accuracy of the pumping was confirmed at ±2% at 0.2 mL/min and above, with the testing carried out with a solution of 80:20 IPA that was pumped at 1000 PSI. The pressure of the pumped solution was also confirmed to be ±2%. These capabilities make it possible to provide pulsation dampening compensation that is a standard feature of this pump.

A pump of this type utilizes canceling pulses through its two heads so as to yield a flow rate that is very stable.

The error in such a pump comes from the flow rate of the liquid analyte (e.g., ethanol) and the capillary properties that are found in a low-density liquid. The surface tension of a liquid is directly related to the capillary properties of that liquid. By way of example but not limitation, the intermolecular forces of ethanol yield a surface tension of $22 \times 10^{-3}$ $J/m^2$ at 25 degrees Celsius. Although this is much lower than water ($72.8 \times 10^{-3}$ $J/m^2$ at 20 degrees Celsius), when this surface tension is combined with the adhesive forces that hold a liquid to the substance that composes the capillary (i.e., PEEK tubing), it can disrupt the consistency of the concentration.

More particularly, it was discovered that, for analyte gasifier (AG) subsystem 10 to produce a 16000 ppm effluent at a 1 LPM gas flow rate at an accuracy of ±29 ppm, the ethanol stream must be pumped at a rate of 80 uL/min. At 80 uL/min, through a 1/16" orifice, it was found that the capillary forces are strong enough to augment the pumping profile and cause a ripple effect that is observable in the ethanol's concentration. Significantly, this was circumvented by the present design which tapers the tip of the PEEK tube that introduces the ethanol into the middle of the carrier gas (e.g., helium) stream.

Additionally, for the highest precision, the apparatus must be able to readily nebulize all of the incoming analyte (e.g., ethanol) in real time. This task is completed by varying the inner diameter of the line that is used to carry the carrier gas (e.g., helium) into volatilization chamber 110. When pumping a solution into a fixed inner diameter line with a highly non-porous surface, the solution is at risk of being deposited onto the sides of the chamber where the flow rate is the slowest and the flow of the gas is most laminar. During initial testing, such anomalies were recognizable when viewing the concentration of the analyte over long run times. To counteract this effect, the sizing of the carrier gas line was stepped down from a 1/4" inner diameter line to a 1/8" inner diameter line. This 1/8" inner diameter line then exited into a chamber that was 2.5" in diameter. The tip of the capillary was positioned at the junction between the 1/4" and 1/8" piping to maximize the wicking of any potential droplets into the gas stream with the increased flow rate and turbulence that an orifice plate transition will create. This increased pressure (16× higher) and flow rate (16× higher) will then dramatically decrease when the AGS enters the heated volatilization chamber. The combination of the extreme temperature as well as the dramatic decrease in pressure while the volume increases work in tandem so as to ensure the proper volatilization of the liquid analyte (e.g., ethanol) into the gaseous state.

More particularly, and looking now at FIG. 9, nebulizer 100 is configured so that:
(i) line 95 has an outer surface which tapers inwardly in the distal direction while the lumen of line 95 remains constant in diameter;
(ii) carrier line 141 has an inner surface which steps down from a larger diameter to a smaller diameter; and
(iii) the distal end of line 95 (i.e., conical tip 143) is disposed adjacent to the location at which the inner surface of carrier line 141 steps down from a larger diameter to a smaller diameter.

In this way, nebulizer 100 provides a complete wicking of the liquid analyte (e.g., ethanol) into the carrier gas (e.g., helium) so that all of the liquid analyte (e.g., ethanol) received from pump module 25 is nebulized.

Volatilization chamber 110 is heated to a temperature sufficiently hotter than the boiling point of the analyte. This ensures that all of the liquid analyte entrained in the carrier gas is volatized. By way of example but not limitation, when the analyte is ethanol, volatilization chamber 110 is preferably heated to approximately 90 degrees Celsius, which is sufficiently hotter than the boiling point of ethanol.

The AGS then flows into expansion chamber 105 via piping 144, where it is allowed to homogenize before flowing out of expansion chamber 105, through pressure adjustment valve 115 and a tube 145 into gas mixer (GM) 15.

Pressure release mechanism 120 is connected to volatilization chamber 110 and is set to a release pressure which is within the pressure limits of the system. Analyte gasifier (AG) subsystem 10 is therefore safe in the event of an excessive pressure buildup in analyte gasifier (AG) subsystem 10.

Gas Mixer (GM) Subsystem 15

Gas mixer 15 receives the AGS from analyte gasifier (AG) subsystem 10, mixes the AGS with other gases, and also provides humidification to the AGS, so as to produce a BGP at a desired concentration with both high accuracy and precision.

Gas mixer (GM) subsystem 15 generally comprises:
(a) a gas analyzer (GA) 146, which monitors the concentration of the AGS arriving from the analyte gasifier (AG) subsystem 10;
(b) a gas proportioner 147 which receives data from gas analyzer (GA) 146 and uses this data to appropriately proportion the flow rates (via flow control valves, see FIG. 1) of (i) the AGS based on any change in its analyte concentration, and (ii) one or more diluent gases (e.g., $O_2$, $CO_2$ and $N_2$), sometimes referred to herein when combined as the "combined diluent gas stream" or "CDGS", which are ultimately to be combined with the AGS;
(c) a humidifier 148 for humidifying the proportioned CDGS exiting the gas proportioner so as to produce a gas stream sometimes referred to herein as the "humidified combined diluent gas stream" or "HCDGS";
(d) a gas mixing tube 149 which receives the proportioned AGS from the gas proportioner 147, and the proportioned HCDGS from the humidifier 148, so as to produce the desired high precision blended gas mixture comprising a volatile analyte (i.e., the BGP); and
(e) a sensor 150 which receives the BGP from gas mixing tube 149 and monitors the concentration of the various constituents of the BGP. If desired, sensor 150 may provide a real-time feedback control which adjusts the amounts of the AGS and the humidified diluent gases that are used to create the BGP so as to compensate for any variations in the concentration of the AGS being produced by analyte gasifier (AG) subsystem 10 so that the final BGP has a concentration of gases that is both highly accurate and precise.

(a) Gas Analyzer (GA) 146

Gas analyzer (GA) 146 receives the AGS from the analyte gasifier (GM) subsystem 10 and monitors the concentration of the analyte in the AGS. Note that it is important to monitor the concentration of the analyte in the AGS since environmental and operational conditions can sometimes cause variations in the concentration of the analyte in the AGS. Examples of such environmental conditions are room temperature, atmospheric pressure, etc. Examples of such operational conditions are system temperature, system pressure, etc. Data from GA 146 is reported to gas proportioner 180 and the AGS is sent to gas proportioner 180. Gas analyzer (GA) 146 is shown in further detail in FIG. 10.

Gas analyzer (GA) 146 analyzes the concentration of the AGS leaving volatilization and expansion chamber module 30 in tube 145. This measurement of the AGS is non-invasive, and the accuracy may be within a few parts per million (PPM), e.g., 30-300 ppm where the analyte is ethanol. In a preferred form of the invention, gas analyzer (GA) comprises a binary gas analyzer and has the capability to measure the ratio of two different gases. By way of example but not limitation, gas analyzer 146 may measure the ratio of ethanol gas to helium gas. Gas analyzer 146 may use spectroscopy, chromatography or other methods in the infrared spectrum or other electromagnetic spectrum bands known to those skilled in the art. In a preferred form of the present invention, gas analyzer 146 uses intensive and/or extensive properties to measure the gas concentrations. For example, gas analyzer 146 may use physical properties including, but not limited to, temperature, pressure, thermal conductivity, flow rate and/or speed of sound measurements to determine the gas concentrations.

Figure 10:
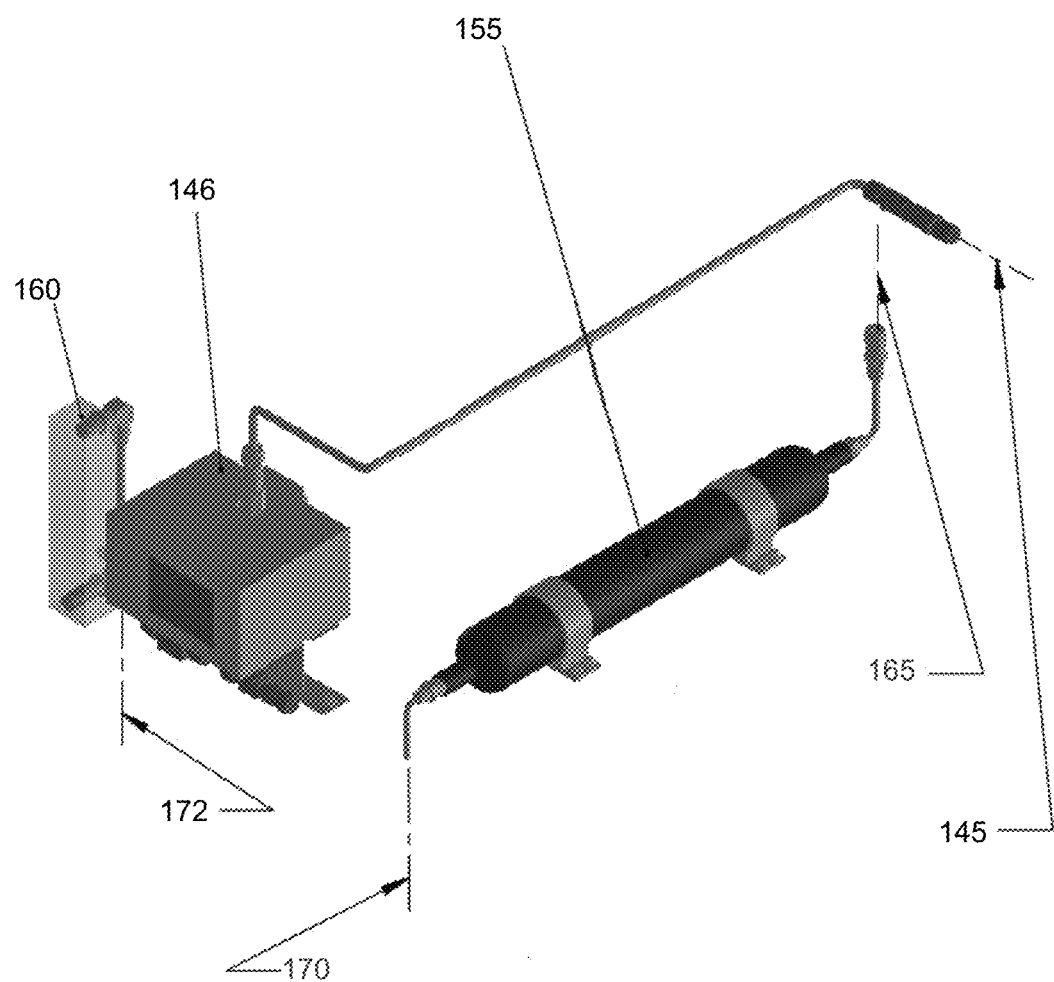
FIG. 10 is a schematic view showing further details of the GA module, as well as additional apparatus.

As shown in FIG. 10, system 5 may also comprise a filter 155 for removing impurities or particulates from carrier gas supply 130, and a flow meter 160 for determining the gas flow rate. This flow meter 160 may be, but is not limited to, a mechanical flow meter, a metering valve or a mass flow controller used as part of a feedback system which uses measurements from the gas analyzer (GA) 146. Where system 5 comprises a filter 155, the carrier gas (e.g., helium) enters filter 155 through an inlet 165 and exits filter 155 through an outlet 170 before it passes into volatilization and expansion chamber module 30 via fitting 135 (see FIG. 6).

(b) Gas Proportioner 147

Gas proportioner 147 uses the data from gas analyzer (GA) 146 to appropriately proportion the flow rates of (i) the AGS based on any change in its analyte concentration, and (ii) one or more diluent gases (e.g., $O_2$, $CO_2$ and $N_2$), sometimes referred to herein when combined as the "combined diluent gas stream" or "CDGS".

In one preferred form of the invention, gas proportioner 147 proportions the flow rates of a source of diluent gas 1 (e.g., $N_2$) 195, a source of diluent gas 2 (e.g., $CO_2$) 200, and a source of diluent gas 3 (e.g., $O_2$) 205. More particularly, gas proportioner 147, using the data received from gas analyzer (GA) 146, proportions the flow rates of the diluent gases as necessary to ultimately produce the desired blended gas product (BGP). Gas proportioner 147 also combines the one or more proportioned diluent gases (e.g., $O_2$, $CO_2$ and $N_2$) into a "combined diluent gas stream" or "CDGS". The proportioned CDGS from gas proportioner 147 is then sent via supply line 207 to humidifier 148.

At the same time, the proportioned AGS is flowed (via supply line 208) to gas mixing tube 149 (see below).

As seen in FIG. 1, gas proportioner 147 uses various flow control valves to adjust the proportions of the AGS, diluent gas 1, diluent gas 2, diluent gas 3, etc. and the CDGS. In one form of the invention, gas proportioner 147 comprises Mass Flow Controllers (MFCs).

(c) Humidifier 148

Humidifier 148 receives the proportioned CDGS from gas proportioner 147 and humidifies the proportioned CDGS to provide a gas stream sometimes referred to herein as the "humidified combined diluent gas stream" or "HCDGS". To this end, humidifier 148 receives water vapor from a source of humidity 210. The HCDGS from humidifier 148 is then sent to gas mixing tube 149 via a supply line 220. Preferably, humidifier 148, source of humidity 210 and gas mixing tube 149 are contained in a temperature-controlled chamber 225.

(d) Gas Mixing Tube 149

Gas mixing tube 149 receives the proportioned AGS from gas proportioner 147 and the proportioned HCDGS from humidifier 148. When the various components are mixed inside of gas mixing tube 149, the result is a high precision blended gas mixture comprising a volatile analyte (i.e., the BGP). The BGP is then sent to sensor 150 via a temperature-controlled supply line 230.

(e) Sensor 150

Sensor 150 receives the BGP from gas mixing tube 149 and analyzes the same, i.e., sensor 150 monitors the concentration of the various constituents of the BGP. And, if desired, data from sensor 150 may be sent back to gas proportioner 147, which then adjusts the flow rates of (i) the AGS, and (ii) the one or more diluent gases (e.g., $O_2$, $CO_2$, and $N_2$), so as to ensure the correct composition of the BGP. Thus, in this form of the invention, gas mixer (GM) subsystem 15 provides a real-time feedback control which adjusts, in real time, the amounts of the AGS and the CDGS that are used to create the BGP so as to compensate for any variations in the concentration of the AGS being produced by the analyte gasifier (AG) subsystem 10 so that the final BGP has a concentration of gases that is both accurate and precise. By way of example but not limitation, when the BGP is to mimic exhaled human breath, sensor 150 adjusts, in real time, the amounts of the AGS and the CDGS that are used to create the BGP so that the final BGP has a concentration of gases that mimics an exhaled human breath so as to provide the desired humidified BGP to a detector to be calibrated and tested (e.g., a breath-based alcohol detector).

It should be appreciated that final feedback of the apparatus may be found with the integration of the apparatus with any of multiple gas-based laboratory grade instruments for sensor 150. Utilizing gas-based laboratory grade instruments for additional tuning of gas proportioner 147 can ensure that any and all errors in the system may be accounted for and managed as needed.

Some Advantages Of The Present Invention

The present invention provides a number of advantages over the prior art. Among other things, the present invention:
provides a system for the creation of humidified organic gas analytes at low concentrations, e.g., concentrations as low as 300 ppm;
can utilize physical constants (i.e., the speed of sound through a gas) to determine the accuracy and precision of an analyte concentration (e.g., a gas analyzer such as a binary gas analyzer) instead of using calibration standards of the analyte (e.g., such as when using pre-filled tanks of an analyte in a carrier gas);
ensures full volatilization of the analyte since the ratios of inner volumes and capillary size are designed to nebulize organics before the heated chamber;
may have a built-in sump to further homogenize analytes to ensure variations from droplet formation and internal flow dynamics are mitigated;
utilizes a continuous bleed valve which allows the gas mixer (GM) subsystem to siphon different volumes of analyte as needed to:
  produce different concentrations of analyte (e.g., ethanol) gas (0.00% BrAC to 0.325% BrAC);
  produce these analyte (e.g., ethanol) concentrations at different flow rates (5.0 LPM to 35.0 LPM); and
  ensure that pressure differentials caused by Mass Flow Controller (MFC) positions (i.e., in the gas proportioner) do not cause pressure differentials that will affect volatilization and overall accuracy and precision;
uses a gas mixing tube which is able to precisely blend the proportioned AGS and the proportioned HCDGS to mimic an exhaled human breath or a specific gas mixture of interest;
uses a gas analyzer and a gas proportioner to adjust the ratio of the gases to account for variations in the analyte gas stream (e.g., ethanol in helium);

humidifies the proportioned CDGS after mixing and before introduction of the AGS, which
yields humidified breath without negatively affecting the concentration of analyte (e.g., ethanol); and
provides both precision and humidification, which are normally very difficult to obtain;
keeps the gas mixture stable and stops water from pulling the analyte (e.g., ethanol) out of the gas phase by heating the humidifier and gas mixing tube to a desired temperature (e.g., 34 degrees Celsius) as well as transportation of the gas mixture through heated lines; and
feeds the output of apparatus 5 through a sensor to confirm the gas mixture's composition and allows for adjustments as needed.

Modifications Of The Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A system for producing a high precision blended gas product (BGP), the system comprising:
   a supply of a volatile analyte in liquid form;
   a supply of an inert carrier gas;
   a supply of at least one diluent gas;
   an analyte gasifier (AG) subsystem for receiving the volatile analyte in liquid form and mixing the volatile analyte with the inert carrier gas so as to form an analyte gas stream (AGS); and
   a gas mixer (GM) subsystem for receiving the AGS from the AG subsystem and mixing the AGS with the supply of at least one diluent gas so as to produce the BGP, wherein the GM subsystem comprises:
      a gas analyzer (GA) for receiving the AGS and analyzing the same;
      a gas proportioner for receiving the AGS from the GA, receiving the at least one diluent gas, and proportioning the AGS and the at least one diluent gas based on the results of the GA so as to provide a proportioned AGS and a proportioned at least one diluent gas; and
      a gas mixing chamber for receiving the proportioned AGS and the proportioned at least one diluent from the gas proportioner so as to produce the BGP.

2. A system according to claim 1 further comprising a temperature-controlled chamber, and further wherein the gas mixing chamber is contained within the temperature-controlled chamber.

3. A system according to claim 1 wherein the volatile analyte comprises ethanol.

4. A system according to claim 1 wherein the inert carrier gas comprises helium.

5. A system according to claim 1 wherein the at least one diluent gas comprises three diluent gases.

6. A system according to claim 5 wherein the three diluent gases comprise $N_2$, $CO_2$ and $O_2$.

7. A system according to claim 6 wherein the gas proportioner proportions the three diluent gases so as to form a combined diluent gas stream (CDGS).

8. A system according to claim 7 wherein the three diluent gases in the CDGS are in a ratio similar to the ratio of the three diluent gases in exhaled human breath.

9. A system according to claim 1 further comprising a humidifier for receiving the proportioned at least one diluent gas from the gas proportioner and for humidifying the proportioned at least one diluent gas before passing the proportioned at least one diluent gas to the gas mixing chamber.

10. A system according to claim 9 wherein the humidifier humidifies the proportioned at least one diluent gas to a humidity level similar to the humidity level in exhaled human breath.

11. A system according to claim 9 further comprising a temperature-controlled chamber, and further wherein the gas mixing chamber and the humidifier are contained within the temperature-controlled chamber.

12. A system according to claim 1 wherein the at least one diluent gas comprises three diluent gases, wherein the three diluent gases comprise $N_2$, $CO_2$ and $O_2$, wherein the gas proportioner proportions the three diluent gases so as to form a combined diluent gas stream (CDGS), wherein the system further comprises a humidifier for receiving the CDGS from the gas proportioner and for humidifying the CDGS before passing the humidified CDGS to the gas mixing chamber.

13. A system according to claim 1 wherein the gas analyzer (GA) comprises a binary gas analyzer (BGA).

14. A system according to claim 1 wherein the gas mixing chamber comprises a gas mixing tube.

15. A system according to claim 1 further comprising a sensor for receiving the BGP from the gas mixing chamber and analyzing the same.

16. A system according to claim 15 wherein the gas proportioner is further configured to proportion the AGS and the at least one diluent gas based on the results of the sensor.

17. A system according to claim 1 wherein the analyte gasifier (AG) subsystem comprises:
   a first tube configured to receive the volatile analyte in liquid form, the first tube having a first portion comprising a distal end, a proximal end, and a lumen extending therebetween, the first portion of the first tube having an outer surface which tapers inwardly in the distal direction;
   a second tube configured to receive the inert carrier gas, the second tube having a second portion comprising a distal end, a proximal end and a lumen extending therebetween, the second portion of the second tube having an inner surface which steps down from a larger diameter to a smaller diameter;
   the second portion of the second tube being disposed coaxially over the first portion of the first tube so that the inner surface of the second portion of the second tube is spaced from the outer surface of the first portion of the first tube; and
   the distal end of the first portion of the first tube is disposed adjacent to the location at which the inner surface of the second portion of the second tube steps down from a larger diameter to a smaller diameter.

18. A method for producing a high precision blended gas product (BGP), the method comprising:
   providing:
      a supply of a volatile analyte in liquid form;
      a supply of an inert carrier gas; and
      a supply of at least one diluent gas;
   mixing the volatile analyte with the inert carrier gas so as to form an analyte gas stream (AGS); and
   mixing the AGS with the supply of at least one diluent gas so as to produce the BGP, wherein the mixing comprises:

analyzing the AGS;

proportioning the AGS and the at least one diluent gas based on the results of analyzing the AGS so as to provide a proportioned AGS and a proportioned at least one diluent gas; and mixing the proportioned AGS and the proportioned at least one diluent so as to produce the BGP.

19. A method according to claim 18 wherein the proportioned AGS and the proportioned at least one diluent gas are mixed in a temperature-controlled environment.

20. A method according to claim 18 wherein the volatile analyte comprises ethanol.

21. A method according to claim 18 wherein the inert carrier gas comprises helium.

22. A method according to claim 18 wherein the at least one diluent gas comprises three diluent gases.

23. A method according to claim 22 wherein the three diluent gases comprise $N_2$, $CO_2$ and $O_2$.

24. A method according to claim 23 wherein the three diluent gases are proportioned so as to form a combined diluent gas stream (CDGS).

25. A method according to claim 24 wherein the three diluent gases in the CDGS are in a ratio similar to the ratio of the three diluent gases in exhaled human breath.

26. A method according to claim 18 wherein the proportioned at least one diluent gas is humidified before being mixed with the AGS.

27. A method according to claim 26 wherein the proportioned at least one diluent gas is humidified to a humidity level similar to the humidity level in exhaled human breath.

28. A method according to claim 26 wherein humidification takes place in a temperature-controlled environment.

29. A method according to claim 28 wherein the at least one diluent gas comprises three diluent gases, wherein the three diluent gases comprise $N_2$, $CO_2$ and $O_2$, wherein the three diluent gases are proportioned so as to form a combined diluent gas stream (CDGS), wherein the CDGS is humidified before mixing with the proportioned AGS.

30. A method according to claim 18 wherein the BGP is analyzed.

31. A method according to claim 30 wherein the proportioning of the AGS and the at least one diluent gas is further based on the analysis of the BGP.

* * * * *